United States Patent [19]

Johnson

[11] Patent Number: 5,009,104
[45] Date of Patent: Apr. 23, 1991

[54] ULTRASONIC CURE MONITORING OF ADVANCED COMPOSITES

[75] Inventor: Delwin O. Johnson, San Diego, Calif.

[73] Assignee: General Dynamics Corporation, San Diego, Calif.

[21] Appl. No.: 443,637

[22] Filed: Nov. 30, 1989

[51] Int. Cl.⁵ .................... G01N 29/16; G01N 9/24
[52] U.S. Cl. .......................... 73/597; 73/599; 73/602; 264/40.1; 264/257; 264/510
[58] Field of Search ................ 73/579, 597, 599, 602, 73/646; 425/174.2; 264/510, 511, 257, 258, 40.1

[56] References Cited

U.S. PATENT DOCUMENTS

| H000,465 | 5/1988 | Brown | 73/599 |
| 2,966,058 | 12/1960 | McSkimin | 73/597 |
| 3,630,307 | 12/1971 | Kamps et al. | 73/599 |
| 4,455,268 | 6/1984 | Hinrichs et al. | 425/174.2 |
| 4,478,072 | 10/1984 | Brown | 73/599 |
| 4,510,103 | 4/1985 | Yamaguchi et al. | 264/40.2 |
| 4,574,637 | 3/1986 | Adler et al. | 73/599 |
| 4,758,803 | 7/1988 | Thomas, III | 264/40.1 |
| 4,780,262 | 10/1988 | Von Vollcli | 264/258 |
| 4,904,080 | 2/1990 | Afromowitz | 73/590 |
| 4,921,415 | 5/1990 | Thomas, III et al. | 425/174.2 |

Primary Examiner—Hezron E. Williams
Assistant Examiner—Rose M. Finley
Attorney, Agent, or Firm—John R. Duncan; Frank D. Gilliam

[57] ABSTRACT

Method and apparatus for the non-destructive monitoring of the time dependent curing of an advanced composite positioned within an autoclave where it is subjected to varying pressures and elevated temperatures over a predetermined time period. A tool receiving the uncured advanced composite for receiving an acoustic wave guide which directly coupled to the composite. Ultrasound pulses are directed through the acoustic wave guide and the amplitude of the reflected pulses indicate changes in the modulus of the composite during the cure.

15 Claims, 1 Drawing Sheet

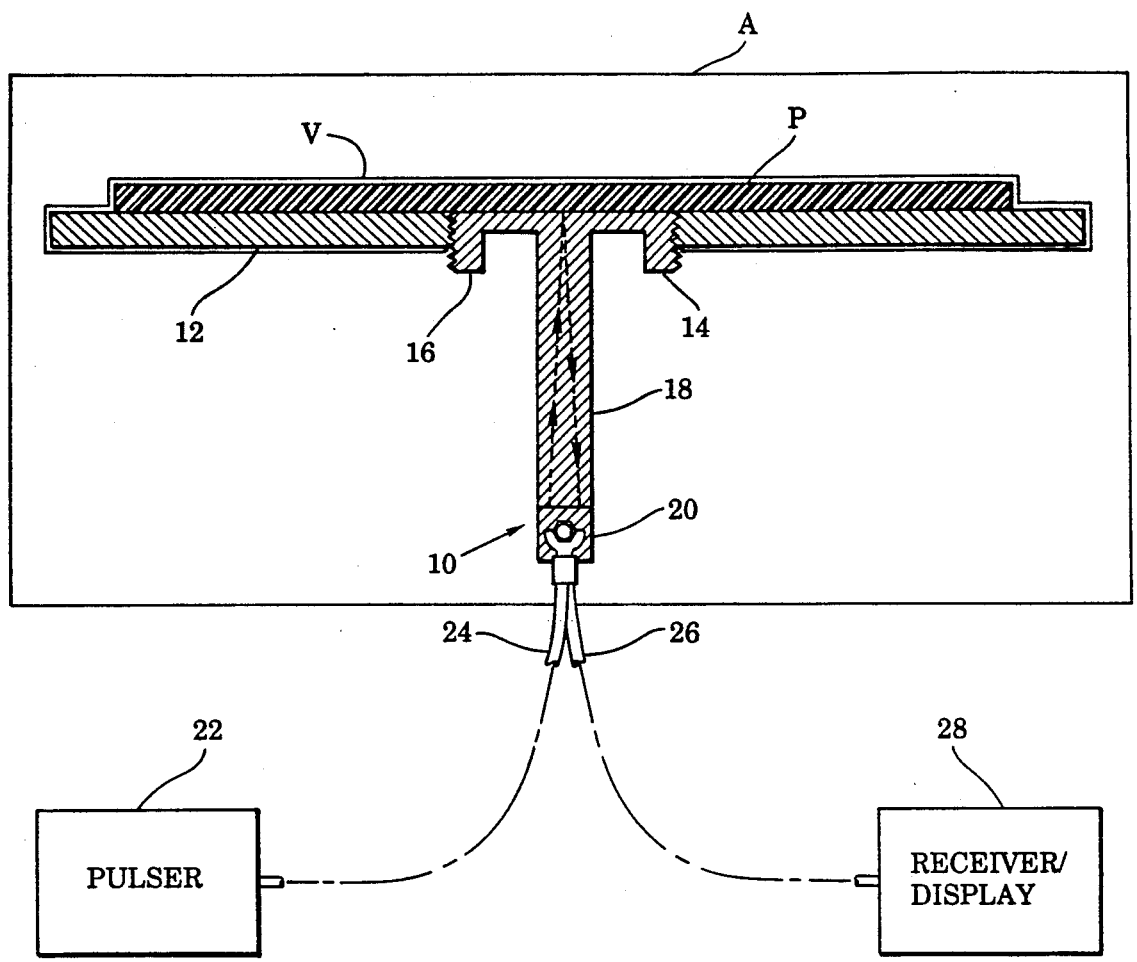
FIG. 1
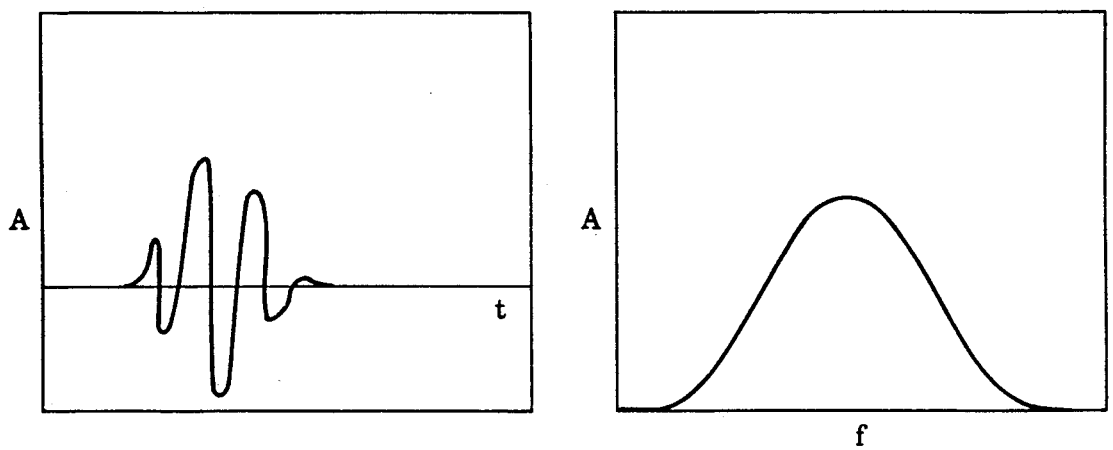
FIG. 2  FIG. 3

ULTRASONIC CURE MONITORING OF ADVANCED COMPOSITES

BACKGROUND OF THE INVENTION

1. Field of the Invention

This invention relates generally to an improvement in the curing of advanced composites in an autoclave and more particularly, but not by way of limitation, to a novel method and apparatus for the ultrasonic monitoring of an advanced composite during the cure cycle within an autoclave.

2. Description of the Prior Art

In the manufacture of advanced composites it is common to position the advanced composite part in an uncured state on a tool such as a bond jig for positioning within an autoclave for curing under pressure and at elevated temperatures. An advances composite may be considered to be a fiber resin matrix that has been formed by hand lay up, filament winding, tape laying or other means. The fiber resin matrix may be formed upon the tool upon which it is to be cured or it may be formed elsewhere and transferred to the tool for curing as in the instance of filament winding. The fiber resin matrix may also be formed by alternating layers of sheet resin with layers of dry fiber that have woven into a fabric or the layers of the woven fiber may be preimpregnated with the resin in an uncured state (prepreg).

In any event the fiber resin matrix, graphite/epoxy being a common one, is positioned on the tool and then covered with a bag made from a flexible plastic material which is sealed to the upper surface of the tool which may be configured in a desired manner by a suitable sealing tape. The bag may be penetrated by instrumentation and a means for drawing a vacuum within the bag so that it closely surrounds the part which may also be covered with various sheets such as breather sheets.

When the tool and the bagged composite part are placed in an autoclave for curing, the composite part is then subjected to a predetermined regimen of pressure and temperature in what is known as a cure cycle. During the cure cycle of the composite part the viscosity of the composite part will vary before it finally hardens into its final shape. If it were possible to determine with sufficient specificity the viscosity of the composite part it would be possible to optimize the cure cycle and to also adjust the cure cycle while the part is being cured to achieve the optimal curing of that particular composite part. This is the general objective of the present invention.

The following patents, which of interest in the general field to which the invention pertain, do not disclose the particular aspects of the invention that are of significant interest.

U.S. Pat. No. 4,478,072 issued on Oct. 23, 1984 to Harold T. Brown discloses an apparatus for determining the concentration of finely divided coal particles dispersed in a fuel oil medium. The apparatus comprises in combination (a) an ultrasonic pulser, (b) an ultrasonic receiver, (c) a gated peak detector, (d) signal conditioning and display circuits and (e) an ultrasonic transducer assembly including a layer of silicone grease interposed between the sample of fuel oil having the coal particles dispersed therein. The pulse generated by the pulser is reflected and the peak amplitude of the reflected pulse is indicative of the solids content of the dispersion. There is no attempt at constant monitoring of a curing composite by monitoring of the viscosity of the composite as is taught by the instant invention.

U.S. Pat. No. 4,574,637 issued on Mar. 11, 1986 to Laszlo Adler et al discloses a method for measuring surface and near surface properties of materials. The properties of the surface layer of a material are measured by a technique which employs the transmission of ultrasonic waves from varying angles of incidence into a specimen, from a transducer at a point spaced from the specimen. The backscattered waves are detected and evaluated from the varying angles to detect the local maximum intensity, from which the corresponding properties of the material are determined. The Adler method induces Raleigh surface waves by varying the incidence of impinging ultrasonic waves. The properties of the surface material are compared to that of the subsurface material. The present invention teaches the application of an ultrasound pulse only perpendicularly to a composite substrate. There is no teaching in Adler, as in the present invention, of the monitoring of a composite part being cured by using reflected ultrasound pulses to determine a change in the viscosity of the composite part.

U.S. Pat. No. 2,966,058 issued on Dec. 27, 1960 to H. J. McSkimin discloses a circuit for the measurement of dynamic properties of materials. The device includes a block of fused silica having a highly polished flat upper surface upon which is positioned a sample of test material. The apparatus then uses dual ultrasonic waves propagated through the silica substrate at different angles to determine various dynamic properties of the test material. This technique while using ultrasound waves does not show ultrasound pulses being directed normally to a curing composite part for the purpose of monitoring the viscosity of the composite part during the cure cycle.

U.S. Pat. No. 3,630,307 issued on Dec. 28, 1971 to Edwin C. Kamps et al for a mechanism and method for measuring sound absorption discloses an electromagnetic tone generator which transmits a tone burst comprising sound waves of known wavelength and intensity into one end of a tube. The other end of the tube is fitted against the surface of a sound attenuation material which reflects the sound waves back along the interior of the tube with a reduction in intensity proportional to the loss of acoustical energy. A microphone is exposed interiorly of the tube at a known distance from each end of the tube. Electronic time delay and gate circuitry feed into a monitoring circuit the electrical oscillations from the microphone produced by a selected series of clear sound waves of the original and the reflected sound bursts for a comparison of amplitudes. The Kamps patent is directed to the reflection of audible sound from a sound attenuation material for the purpose of determining its degradation during use. It is not directed to the use of ultrasound energy to monitor changes in the modulus of a composite part as it is being subjected to a cure cycle within an autoclave.

U.S. Pat. No. 4,510,103 issued Apr. 9, 1985 to Yasuhiro Yamaguchi et al relates to a method of molding a composite material containing a thermosetting resin by determining an optimum pressureinitiating time from abrupt variations in the electric capacity and/or dielectric loss coefficient of the molded material caused by the application of heat to the composite material. The purpose of this patent is only to determine the point at which to apply pressure to a mold rather than to continually monitor the viscosity of a curing composite part.

U.S. Pat. No. 4,145,912 issued Mar. 27, 1979 to Jacques L. P. Hognat relates to a method and apparatus and apparatus for measuring visco-elasticity of composite sheet material. This patent involves heating a sample of the sheet material comprising a flexible organic and-/or inorganic reinforcement impregnated with a synthetic resin and stretching the sample while a reciprocal movement is applied to the sample. Variations in the amplitude of motion received at the other end are observed.

SUMMARY OF THE INVENTION

In accordance with a preferred embodiment of the present invention, there is provided a method and apparatus for monitoring the time dependent curing of an advanced composite part that is positioned within an autoclave where it is subjected to varying pressure and temperature over a period of time in a predetermined cure cycle. The invention contemplates positioning an uncured advanced composite secured within a vacuum bag and carried by a tool such as a bond jig. The tool is provided with an aperture for accommodating an acoustic wave guide that is directly coupled to the part. Pulses of ultrasound energy are directed through the wave guide and the amplitude of the pulses of reflected ultrasound energy are monitored to determine if there has been a change in the modulus of composite part during the cure cycle. The cure cycle may be optimized in this manner and may be adjusted as desired during the cycle as desired.

Other features and attendant advantages of the present invention will become apparent to those skilled in the art from a reading of the following detailed description constructed in accordance with the accompanying drawings and wherein:

BRIEF DESCRIPTION OF THE DRAWINGS

FIG. 1 is a diagrammatic representation of apparatus for the ultrasonic cure monitoring of an advanced composite constructed in accordance with the principles of the present invention.

FIG. 2 is a diagram illustrating the plotting of amplitude of a waveform against time.

FIG. 3 is a diagram illustrating the plotting of amplitude of a waveform against frequency.

DESCRIPTION OF THE PREFERRED EMBODIMENT

The propagation of an ultrasonic wave trough a medium is dependent upon the bulk properties of the medium, including density and modulus. This allows one to monitor the bulk properties of a composite part during cure in an autoclave. The cure monitoring technique of the present invention will allow an autoclave operator to make informed decisions during the course of the cure.

For ease in understanding the invention it would be helpful to briefly review certain ultrasonic fundamentals. There are three basic parameters that characterize an ultrasonic waveform: the time domain amplitude, the frequency distribution, and the velocity of the waveform. The waveform is typically presented in the time domain, where the amplitude is plotted as a function of time, as in FIG. 2. The frequency distribution is identified by measuring the amplitude as a function of frequency, as in FIG. 3. This is commonly done by applying a Fast Fourier Transform to the time domain waveform. Velocity is measured by comparing the time position of the waveform before and after it propagates through the test sample. The time difference is the time of flight. The velocity of the wave is calculated by dividing the sample thickness by the time of flight.

There are two principal modes of ultrasonic propagation: shear and compressional. Solids will readily propagate both modes, however liquids and gases are not capable of generating nor maintaining tangential stresses and therefore do not propagate shear waves.

In the past attempts have been made to monitor the curing of advanced composites in an autoclave with ultrasonics. A waveform was generated by exciting a piezoelectric crystal with an electric pulse. The concept was to apply a waveform to one surface of the composite part to propagate a compressional wave through the composite part and to monitor the attenuation of the time domain waveform amplitude as it passed through the part. It was believed that where the received waveform amplitude (assuming a constant source amplitude) would be proportional to the logarithm of the complex viscosity of the composite part being cured.

Unfortunately this concept did prove to be successful in practice as there was no quantitative theoretical support for the proposed relationship between amplitude and viscosity. Further, attenuation of the waveform was strongly dependent up the thickness of the sample, which thickness does vary during the cure. Since the pulsing transducer applying the pulse and the receiving transducer must both "wet out" or be in contact with the part during cure, it was found difficult to maintain this contact when the thickness of the part varied during cure. The upper transducer had to pierce the vacuum bagging material and had to be located directly above the lower transducer. Since the output from this arrangement was only qualitative, it was found that the reproducibility of results was poor. Also, shear waves cannot be used and even compressional waves are overwhelmingly attenuated at minimum viscosity.

Building upon this past effort which was not successful the present invention of monitoring the cure of composites in an autoclave with ultrasonics has been devised and provides improved accuracy and reproducibility over prior art methods. The present invention has eliminated the shortcomings associated with the use of an upper transducer and is supported with quantitative theory, rather than empirical relationships.

The present invention uses to advantage the effect of the surface boundary between the pulsing transducer and the curing composite part. When a wave, propagating in any medium, passes through a surface boundary into another medium, a portion of the energy is transmitted into the second medium, while the remaining energy is reflected back. The transmissivity and reflectivity of the surface boundary are functions of the acoustic impedances of the two media:

$$A_t/A_i = 2R_1/(R+R_2)$$

$$A_r/A_i = (R_1-R_2)/(R_1+R_2)$$

where:
$A_i$ = incident waveform amplitude
$A_t$ = transmitted waveform amplitude
$A_r$ = received waveform amplitude
$R_1$ = acoustic impedance of the first medium
$R_2$ = acoustic impedance of the second medium Acoustic impedance is equal to the product of the density of the medium and the ultrasonic velocity through the medium, and modulus is equal to the density of the medium multiplied by the square of the velocity:

$$R = pc$$

$$M = pc^2$$

where M represents either shear or longitudinal compressional modulus. The appropriate modulus is determined by whether one propagates shear or compressional ultrasonic waves.

Referring now to FIG. 1, the reference character 10 generally illustrates an apparatus constructed in accordance with a preferred embodiment of the instant invention for the ultrasonic monitoring of the curing of advanced composites in an autoclave. A suitable tool such as bond jig 12 is provided for receiving an uncured composite part P that may be formed of a fiber resin matrix such as graphite/epoxy. The part P may be formed by hand layup, filament winding of another mandrel, tape layup or any other desired method of material deposition. For ease of illustration, a vacuum bag for sealing the part P against the tool 12 is shown positioned within autoclave A for heat curing of the composite. Instrumentation, and other aspects of curing an advanced composite part within the autoclave have been eliminated for ease of illustration but suffice it to say all such details are readily within the skill of one experienced in the art of manufacturing advanced composites.

The tool 12 is provided with a large aperture 14 which is threaded to threadedly receive a large annular disc member 16 which is formed at one end of metal rod member 18 which acts as a waveguide for ultrasonic pulses. A suitable crystal 20 is permanently attached to the end of the waveguide 18 at the end opposing the disc member 16. Since the disc member 16 is threadedly mounted in the tool 12, it may be precisely adjusted into contact with the part P. This may be readily accomplished by laying a straightedge on the surface of the tool and adjusting the disc member 16 within the threaded aperture 14 until it is suitable contact with the part. This prevents decoupling due to a recessed disk member 16 or marring of the part P by a protruding disk member 16. A suitable tacky tape, not shown, may be used to seal around the threads on the bottom of the tool 12.

Referring again to the waveguide 18, the length of the rod 18 allows the crystal 20 to stop ringing before the reflected wave form is received. For example, if the waveguide is 10 cm long and constructed of aluminum then the total waveform travel time is:

$$2 \times 10 \text{ cm} / 5 E + 05 \text{ cm sec}^{-1} = 0.04 \text{ msec}$$

A crystal 20 should in that instance be selected that stops ringing after 0.02 msec. This allows a received waveform to be cleanly separated from the pulsing waveform.

It should be noted that it is important that the waveguide 18 does not unnecessarily scatter the waveform. Thus, the threads of the threaded connection of the disc 16 to the tool 12 ant the tool 12 itself are isolated from the waveguide 18 by the wide thin disc member 16. Thus, virtually none of the waveform energy will be lost by lateral scattering.

A suitable pulser 22 that is connected to the crystal by high temperature resistant shielded cable 24 provided a source of ultrasonic pulses. An ultrasonic pulse is transmitted by the crystal 20 through the waveguide 18 where it impinges upon one side of the part P as indicated by the dashed line. The reflected pulse also shown by dotted line is received back at the end of the waveguide 18 and transmitted via a similar cable 26 to a suitable receiver/ display 28 where the amplitude of the received reflected ultrasonic pulse may be suitably displayed.

The concept of the present invention, which may be accomplished by the arrangement of FIG. 1, is that by measuring the amplitude of the received waveform, and by knowing the density of the composite part, one can calculate the modulus of the composite part P. Only the wave reflected from the surface of the part P is of concern since the wave energy transmitted through the surface boundary of the part P is not measured. The novel method of the present invention offers the following advantages over the through transmission method using ultrasonics of the prior art. This invention is supported by quantitative theory. One transducer is used and it is supported in the tool 12 rather than in the bagging material. The waveform environment is 100% controlled. The measured waveform never leaves the calibrated waveguide 18. This also allows for shear waves, since the medium, which in the illustration is aluminum, is always a solid. The required sensor "wet out" is more easily obtained as there is only one sensor and it is located underneath the part P.

The arrangement 10 is calibrated by measuring the received waveform amplitude with air ($R_2 \rightarrow 0$) and water ($R_2$=known constant) being the test samples. In the case of air as the second medium, the reflectivity is virtually 100%. This is the maximum possible received waveform amplitude. After measuring the reduced amplitude with water being the second medium, one can now calculate the acoustic impedance of the waveguide 18 ($R_2$). The general surface boundary effect is to reflect very little energy if the two mediums have similar acoustic impedances. When the impedances differ, then larger portions of the wave energy is reflected. Since the ultrasonic waveguide 18 is virtually constant, any changes is the received waveform amplitude indicate a change in the acoustic impedance of the second medium, namely the composite part P. Assuming the acoustic impedance of the waveguide 18 to be greater than that of the composite part P, one would expect a maximum received amplitude at minimum viscosity. Thus, by observing the amplitude of the received waveform on the display 28 an experienced operator may detect changes in the viscosity of the part P as it cures and make informed decisions during the course of the cure such as increasing the temperature within the autoclave.

Although the present invention has been shown and described with reference to a particular embodiment, nevertheless, various changes and modifications obvious to one skilled in the art to which the invention pertains are deemed within the purview of the invention.

What is claimed is:

1. A non-destructive method for monitoring the time dependent curing of an advanced composite positioned within an autoclave where it is subjected to varying pressure and temperature over a predetermined period of time, which method comprises:

positioning an uncured advanced composite secured within a vacuum bag and carried by a tool within an autoclave;

varying the heat and pressure within the autoclave over a predetermined period of time to cure the composite;

coupling an acoustic waveguide to one side of the uncured advanced composite by extending said acoustic waveguide through an aperture provided in said tool so that the wave guide may be directly coupled to a surface of the composite;

directing a pulse of ultrasound energy through the waveguide to the side of the advanced composite; and analyzing the ultrasound energy reflected from the side of the advanced composite to determine the modulus of the advanced composite at a particular point in its curing.

2. The method of claim 1 wherein the acoustic wave guide is placed in contact with the side of the uncured composite that is in contact with the tool.

3. The method of claim 3 wherein the acoustic wave guide comprises a solid metal rod having a flat member provided at one end that is adapted to be coupled to the composite.

4. The method of claim 3 wherein the flat member is snugly and adjustably positioned within the aperture of the tool for coupling to the composite.

5. The method of claim 4 wherein the solid rod portion of the acoustic wave guide has a pulsable crystal positioned at the end opposing the flat member whereby a pulse of ultrasound energy is generated at one end of the wave guide and guided to the flat member coupled to the composite.

6. The method of claim 1 wherein:

the step of analyzing the reflected ultrasound energy comprises repeatedly measuring the amplitude of the waveform of the reflected ultrasound energy to determine whether the modulus of the composite has changed.

7. The method of claim 2 which further includes the step of changing the temperature within the autoclave in response to changes in the modulus of the composite.

8. An arrangement for the non-destructive monitoring of the time dependent curing of an advanced composite positioned within an autoclave where it is subjected to varying pressures and elevated temperatures over a period of time, which arrangement comprises:

a tool adapted to receive an advanced composite and a vacuum bag encompassing the advanced composite on one surface thereof;

acoustic wave guide means operatively coupled to one surface of the composite;

means to repeatedly generate ultrasound pulses at one end of the acoustic wave guide for application to the surface of the advanced composite; and means to observe the amplitude of the ultrasound pulses reflected from the surface of the advanced composite whereby changes in the modulus of the advanced composite may be monitored.

9. The arrangement set forth in claim 8 wherein:

the tool is provided with an aperture that extends through the tool in the area receiving the composite.

10. The arrangement set forth in claim 9 wherein:

the acoustic wave guide means extends through said aperture in the tool for coupling to the advanced composite.

11. The arrangement set forth in claim 10 wherein:

the aperture in the tool has a threaded annular shape.

12. The arrangement set forth in claim 11 wherein:

the acoustic wave guide means includes a metal rod member having a flat disc member provided at one for being threadedly positioned within the aperture in the tool.

13. The arrangement set forth in claim 12 wherein:

the means to repeatedly generate ultrasound pulses includes a crystal secured to the end of the rod member opposing the flat disk member.

14. The arrangement set forth in claim 13 wherein: the length of the rod member of the acoustic wave guide is sufficiently long to permit the crystal to stop ringing before the waveform of the reflected pulse is received from the surface of the advanced composite.

15. The method of claim 1 wherein the acoustic wave guide is removably coupled to said surface of said composite.

* * * * *